United States Patent [19]

Thym et al.

[11] 4,098,810

[45] Jul. 4, 1978

[54] N-(FLUORODICHLOROMETHYLTHIO)-BENZANILIDES

[75] Inventors: Sabine Thym, Ludwigshafen; Ernst-Heinrich Pommer, Limburgerhof; Bernd Zeeh; Friedrich Linhart, both of Ludwigshafen, all of Fed. Rep. of Germany

[73] Assignee: BASF Aktiengesellschaft, Ludwigshafen, Fed. Rep. of Germany

[21] Appl. No.: 770,226

[22] Filed: Feb. 18, 1977

[30] Foreign Application Priority Data

Mar. 20, 1976 [DE] Fed. Rep. of Germany ....... 2611902

[51] Int. Cl.$^2$ .................... C07C 69/00; A01N 9/12

[52] U.S. Cl. .................... 260/453 RW; 424/298

[58] Field of Search .................... 260/453 RW; 424/298

[56] References Cited

FOREIGN PATENT DOCUMENTS 2,557,950  8/1976  Fed. Rep. of Germany ....... 260/453 RW

*Primary Examiner*—Elbert L. Roberts
*Assistant Examiner*—Robert C. Whittenbaugh
*Attorney, Agent, or Firm*—Keil, Thompson & Shurtleff

[57] ABSTRACT

New and valuable N-(fluorodichloromethylthio)-benzanilides, a process for their manufacture, fungicides containing these compounds as active ingredients, and a method of combatting fungi with these compounds.

3 Claims, No Drawings

N-(FLUORODICHLOROMETHYLTHIO)-BENZANILIDES

The present invention relates to new N-(fluorodichloromethylthio)-benzanilides, a process for the manufacture of these compounds, fungicides containing these compounds, and their use as fungicides.

It is known to use 2-substituted benzanilides, e.g., 2-methyl-, 2-chloro-, 2-bromo- and 2-iodobenzanilide, for combatting phytopathogenic fungi (German Laid-Open Application DOS No. 1,642,224). However, their action is poorer than that of the new compounds.

We have now found that N-(fluorodichloromethylthio)-benzanilides of the formula

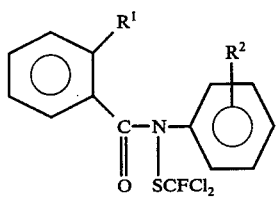

where $R^1$ denotes halogen (fluoro, chloro, bromo, iodo), optionally halogen-substituted alkyl of 1 to 4 carbon atoms, and $R^2$ denotes hydrogen, halogen or optionally substituted saturated or unsaturated alkyl or alkoxy, have a better and broader fungicidal action than the prior art active ingredients.

Examples of meanings for $R^1$ are methyl, ethyl, propyl, isopropyl and butyl.

Examples of meanings for $R^2$ are fluorine, chlorine, bromine, iodine, and especially alkyl of 1 to 8, preferably 1 to 6, carbon atoms optionally substituted by -O-, -S- or

in the alkyl chain or CN, A denoting alkyl of 1 to 4 carbon atoms.

The new compounds are obtained by reacting benzanilides of the formula

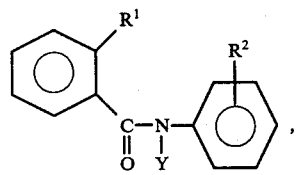

where $R^1$ and $R^2$ have the above meanings and Y denotes hydrogen or a metal atom (sodium, potassium), with a sulfenyl chloride of the formula

preferably in stoichiometric amounts or with the sulfenyl chloride in a slight excess. When Y is hydrogen, it is advantageous for an acid-binding agent to be present in order to facilitate and accelerate the reaction.

When 2-chlorobenzanilide, fluorodichloromethylsulfenyl chloride and pyridine are used, the reaction of the process according to the invention may be represented by the following scheme:

Reaction 1:

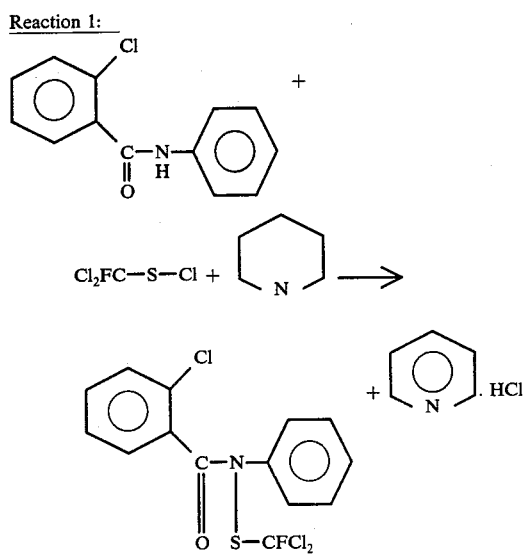

or, when the sodium salt of 2-chlorobenzoic acid-3'-fluoroanilide is used, by the following scheme:

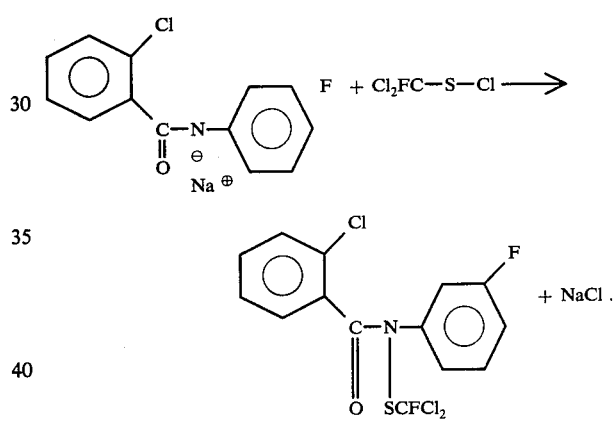

The temperatures for the reactions according to the invention may vary over a wide range; the range from −10° to +100° C is preferred.

Diluents include water, inert organic solvents such as benzene, toluene, chlorobenzene, cyclohexane, petroleum ether, tetrahydrofuran, dioxane, methylene chloride, chloroform, ethyl acetate, acetone, or mixtures of these solvents. When Y is a metal atom, it may occasionally be advisable, for a homogeneous reaction, to employ polar aprotic diluents such as acetonitrile, dimethylformamide, N-methylpyrrolidone, dimethyl sulfoxide, sulfolane, and hexamethylphosphoric triamide. To bind the hydrogen chloride liberated in reaction 1, it is advantageous to add a tertiary organic base such as pyridine, quinoline, triethylamine, dialkylcyclohexylamine, alkali metal bicarbonate, alkali metal carbonate or alkali metal hydroxide, e.g., sodium carbonate, potassium carbonate, sodium hydroxide and potassium hydroxide, in the amount necessary for the reaction.

The active ingredients according to the invention have a strong fungitoxic action on injurious fungi, for example phytopathogenic fungi, especially of the Basidiomycetes class, e.g., Puccinia types in cereals, Uromyces types in beans, *Hemileia vastatrix* in coffee, *Exobasidium vexans* in tea, rusts in poplars and ornamentals, Rhizoctonia types, *Sclerotium rolfsii,* Corticium types, *Coniophora puteana,* Merulius types, *Polystoctus versicolor,* and *Lentinus lepideus.*

Examples of other fungus classes are *Plasmopara viticola* in grapes, *Erysiphe graminis* in cereals, *Botrytis cinerea* in grapes, strawberries, ornamentals and Solanaceae, *Aspergillus niger, Pullularia pullulans, Chaetomium globosum, Humicola grisea, Sclerophoma pityophila,* and fungi which destroy or discolor wood. The active ingredients according to the invention, especially the compounds fluoro-substituted in the aniline radical, also have a herbicidal action on dicotyledonous weeds.

The fungicidal agents contain from 0.1 to 95, preferably from 0.5 to 90, wt% of active ingredient. The application rates depend on the type of effect to be achieved, and range from 0.001 to 3 kg and more, but preferably from 0.01 to 1 kg, of active ingredient per hectare.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entriely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

When the active ingredients are used for protecting materials, e.g., as fungicides for paints, application rates are from 0.5 to 5% of active ingredient, based on the total weight of the paints to be preserved. The new active ingredients may also be employed as fungicidally active components of oil-based wood preservatives for protecting wood against fungi which destroy or discolor wood. The wood is treated with the agents for instance by impregnation or painting.

The active ingredients may also be mixed with other prior art fungicides. In many instances, the fungicidal spectrum is increased; a number of these fungicide compositions also exhibit synergistic effects, i.e., the fungicidal effectiveness of the combination product is greater than that of the individual components combined.

The following list of fungicides with which the N-(fluorodichloromethylthio)-benzanilides of the invention may be combined is intended to illustrate, but not restrict, possible combinations:

ferric dimethyldithiocarbamate (ferbam)
zinc dimethyldithiocarbamate (ziram)
manganese ethylenebisdithiocarbamate (maneb)
zinc ethylenebisdithiocarbamate (zineb)
tetramethylthiuram disulfide (thiram)
manganese-zinc ethylenediamine-bisdithiocarbamate (mancoceb)
zinc-(N,N'-propylene-bisdithiocarbamate) (propineb)
ammonia complex of zinc-(N,N'-ethylene-bisdithiocarbamate) and N,N'-polyethylene-bis-(thiocarbamoyl)-disulfide (metiram)
ammonia complex of zinc-(N,N'-propylene-bisdithiocarbamate) and N,N'-polypropylene-bis-(thiocarbamoyl)-disulfide (methyl-metiram)
3,5-dimethyl-1,3,5-2H-tetrahydrothiadiazine-2-thione
dinitro-(1-methylheptyl)-phenylcrotonate (dinocap)
2-sec-butyl-4,6-dinitrophenyl-3,5-dimethylacrylate (binapacryl)
2-sec-butyl-4,6-dinitrophenylisopropylcarbonate;
2,4,5-trichlorophenol
pentachlorophenol (PCP)
barium salt of pentachlorophenol (5 B)
pentachlorophenyl acetate
pentachlorobenzyl alcohol
di-(5-chloro-2-hydroxyphenyl)-methane (dichlorophen)
phenyl-(5-chloro-2-hydroxyphenyl)-methane
N-trichloromethylthiotetrahydrophthalimide (captan)
N-trichloromethylthiophthalimide (folpet)
N-fluorodichloromethylthio phthalimide
N-(1,1,2,2-tetrachloroethylthio)-tetrahydrophthalimide (captafol)
2-heptadecyl-2-imidazoline (glyodin)

2,4-dichloro-6-(o-chloroanilino)-s-triazine (anilazin)
diethylphthalimidophosphorothioate (plondrel)
5-amino-1-[bis-(dimethylamino)-phosphynyl]-3-phenyl-1,2,4-triazole   5-ethoxy-3-trichloromethyl-1,2,4-thiadiazole
2,3-dicyano-1,4-dithiaanthraquinone (dithianon)
2-thio-1,3-dithio-[4,5-b]-quinoxaline (thioquinox)
methyl 1-(butylcarbamoyl)-2-benzimidazolecarbamate (benomyl)
2-methoxycarbonylaminobenzimidazole
2-thiocyanomethylthiobenzothiazole (busan)
4-(2-chlorophenylhydrazono)-3-methyl-5-isoxazolone
1-(1,2,4-triazolyl-1')-[1-(4'-chlorophenoxy)]-3,3-dimethylbutan-2-one (triadimefon)
1-(1-imidazoyl)-2-allyloxy-2-(2,4-dichlorophenyl)-ethane (imazalil)
2-(O,O-diethylthionophosphoryl)-5-methyl-6-carbethoxypyrazolo-(1,5a)-pyrimidine (pyrazaphos)
pyridine-2-thiol-1-oxide
8-hydroxyquinoline and its copper salt
5,5-dimethyl-3-(3,5-dichlorophenyl)-2,4-dioxo-1,3-oxazolidine
5-methyl-5-vinyl-3-(3,5-dichlorophenyl)-2,4-dioxo-1,3-oxazolidine
2-[furyl-(2)]-benzimidazole
piperazine-1,4-diyl-bis[1-(2,2,2-trichloroethyl)-formamide](triforine)
2-[thiazolyl-(4)]-benzimidazole
5-butyl-2-dimethylamino-4-hydroxy-6-methylpyrimidine (dimethirimol)   bis-(p-chlorophenyl)-3-pyridinemethanol
1,2-bis-(3-ethoxycarbonyl-2-thioureido)-benzene (thiophanate)
1,2-bis-(3-methoxycarbonyl)-2-thioureido)-benzene (thiophanate M)
dodecylguanidine acetate (dodine)
3-[2-(3,5-dimethyl-2-oxycyclohexyl)-2-hydroxyethyl]-glutarimide (cycloheximide)
hexachlorobenzene
N-dichlorofluoromethylthio-N',N'-dimethyl-N-phenyl-sulfuric acid
diamide (dichlorfluanid)
N-dichlorofluoromethylthio-N-methyl-N'-methyl-N'-phenylsulfuric acid diamide
2,4,5,6-tetrachloroisophthalonitrile (daconil)
1-(3,4-dichloroanilino)-1-formylamino-2,2,2-trichloroethane (chloraniformethan)
2,6-dimethyl-N-tridecylmorpholine and its salts
2,6-dimethyl-N-cyclododecylmorpholine and its salts
2,3-dichloro-1,4-naphthoquinone
1,4-dichloro-2,5-dimethoxybenzene
p-dimethylaminobenzenediazosodium sulfonate
2-chloro-1-nitropropane
polychloronitrobenzenes, such as pentachloronitrobenzene,
methyl isothiocyanate, triphenyl tin acetate (fentin acetate),
fungicidal antibiotics such as griseofulvin and kasugamycin, tetrafluorodichloroacetone, 1-phenylthio semicarbazide,
N-nitrosocyclohexylhydroxylamine and its aluminum salt (fungol) Bordeaux mixture, nickel-containing compounds and sulfur.

These agents may be added to the fungicides according to the invention in a weight ratio of from 1:10 to 10:1.

If desired, they may also be added immediately before application (tankmix).

EXAMPLE 1

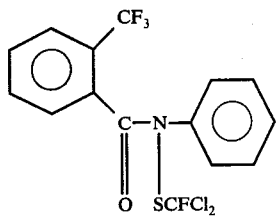

N-(fluorodichloromethylthio)-2-trifluoromethylbenzanilide 14 parts (by weight) of fluorodichloromethylsulfenyl chloride in 50 parts of methylene chloride, and 3 parts of pyridine in 50 parts of methylene chloride are dripped, with ice cooling, into 20 parts of 2-trifluoromethylbenzanilide in 200 parts of methylene chloride in such a manner that the temperature does not exceed 5° C. The temperature of the mixture is allowed to rise to room temperature, and it is then extracted with water, dried, and concentrated in vacuo to dryness. The residue (27 parts) is recrystallized from n-hexane, m.p.: 91° – 92° C.

The following compounds for instance are obtained analogously from the corresponding benzanilides:

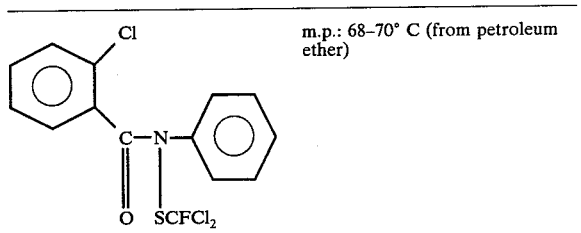

m.p.: 68–70° C (from petroleum ether)

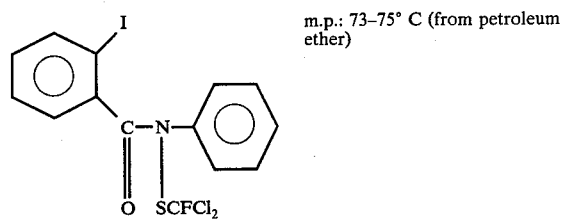

m.p.: 73–75° C (from petroleum ether)

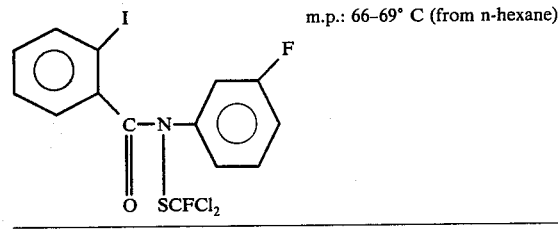

m.p.: 66–69° C (from n-hexane)

EXAMPLE 2

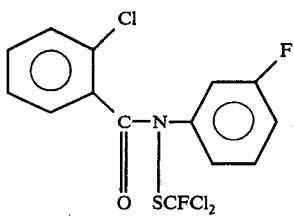

N-(fluorodichloromethylthio)-2-chlorobenzoic acid-3'-fluoroanilide 20 parts of 2-chlorobenzoic acid-3'-fluoroanilide is heated in 200 parts of toluene at 90° - 100° C. 3 parts of sodium hydride is added and the mixture heated for a further 2 hours at 90° C. After the mixture has been cooled to 0° C, 17 parts of fluorodichloromethylthiosulfenyl chloride is added, with ice cooling, in such a manner that the temperature does not exceed 5° C. The temperature of the mixture is allowed to rise to room temperature, and the mixture is then suction filtered, and concentrated to dryness in vacuo. The residue (30 parts) is recrystallized from n-hexane, m.p.: 81° - 84° C.

The following compounds for instance are obtained analogously from the sodium salts of the corresponding benzanilides:

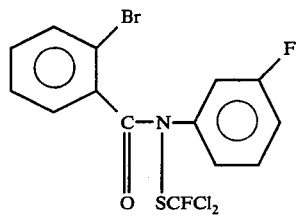  m.p.: 88–91° C (from n-hexane)

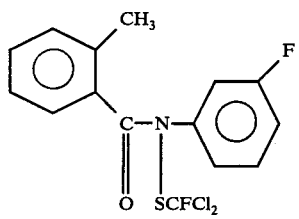  m.p.: 46–48° C (from n-pentane)

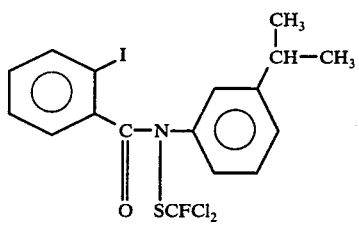  m.p.: 63–66° C (from n-hexane)

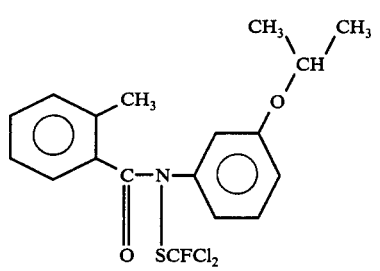  m.p.: 45–48° C (from n-pentane)

EXAMPLE 3

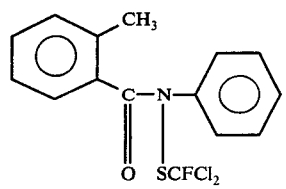

N-(fluorodichloromethylthio)-2-methylbenzanilide 21 parts of 2-methylbenzanilide and 10 parts of pyridine are dissolved in 150 parts of toluene. 17 parts of fluorodichloromethylsulfenyl chloride is dripped in in such a manner that the temperature rises to 30° C. After the mixture has been heated for 3 hours at 60° C, it is cooled, washed with water, dried, and concentrated to dryness in vacuo. The reaction product remains as a crystalline residue (33 parts), m.p.: 56° - 58° C.

The following compound for instance is obtained analogously from the corresponding benzanilide:

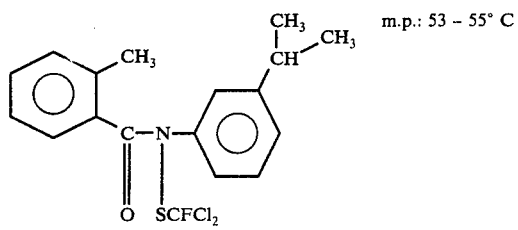  m.p.: 53 - 55° C

EXAMPLE 4

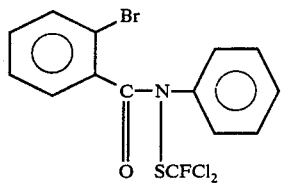

N-(fluorodichloromethylthio)-2-bromobenzanilide 51 parts of N,N-dimethylcyclohexylamine is added to a solution of 55 parts of 2-bromobenzanilide in 150 parts of toluene. With ice cooling, 51 parts of fluorodichloromethylsulfenyl chloride is slowly dripped in between 20° and 30° C. After suction filtration and concentration in vacuo to dryness, the residue (93 parts) is recrystallized from petroleum ether, m.p.: 80° - 83° C.

The following compound for instance is obtained analogously from the corresponding benzanilide:

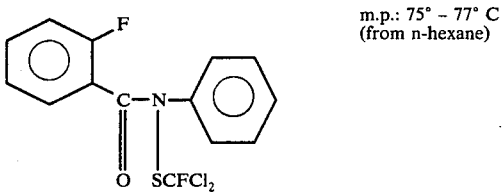  m.p.: 75° - 77° C (from n-hexane)

Some of the N-(fluorodichloromethylthio)-benzanilides obtainable by the process according to the invention are listed in the following table:

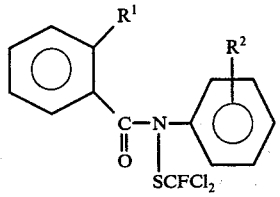

| Compound No. | R¹ | R² | m.p. (° C) |
|---|---|---|---|
| 1 | CH₃ | H | 56 – 58 |
| 2 | CH₃ | 3-i-C₃H₇ | 53 – 55 (from n-pentane) |
| 3 | CH₃ | 3-t-C₄H₉ | 65 – 66 (from n-pentane) |
| 4 | CH₃ | 3-O-i-C₃H₇ | 45 – 48 (from n-pentane) |
| 5 | CH₃ | 2-F | 68 – 70 (from n-pentane) |
| 6 | CH₃ | 3-F | 46 – 48 (from n-pentane) |
| 7 | CH₃ | 4-F | 71 – 73 (from n-pentane) |
| 8 | F | H | 61 – 63 (from cyclohexane) |
| 9 | F | 3-F | 73 – 75 (from n-hexane) |
| 10 | Cl | H | 68 – 70 (from petroleum ether) |
| 11 | Cl | 3-i-C₃H₇ | 60 – 63 (from n-pentane) |
| 12 | Cl | 3-t-C₄H₉ | 63 – 65 (from n-pentane) |
| 13 | Cl | 3-O-i-C₃H₇ | |
| 14 | Cl | 2-F | 90 – 91 (from n-hexane) |
| 15 | Cl | 3-F | 81 – 84 (from n-hexane) |
| 16 | Cl | 4-F | 89 – 91 (from n-hexane) |
| 17 | Br | H | 80 – 83 (from petroleum ether) |
| 18 | Br | 3-i-C₃H₇ | 76 – 80 (from n-hexane) |
| 19 | Br | 3-t-C₄H₉ | 76 – 80 (from n-pentane) |
| 20 | Br | 3-O-i-C₃H₇ | |
| 21 | Br | 2-F | 90 – 91 (from n-hexane) |
| 22 | Br | 3-F | 88 – 91 (from n-hexane) |
| 23 | Br | 4-F | 64 – 66 (from n-hexane) |
| 24 | I | H | 73 – 75 (from petroleum ether) |
| 25 | I | 3-i-C₃H₇ | 63 – 66 (from n-hexane) |
| 26 | I | 3-t-C₄H₉ | 79 – 83 (from n-pentane) |
| 27 | I | 3-O-i-C₃H₇ | 91 – 93 (from n-pentane) |
| 28 | I | 2-F | 77 – 79 (from n-hexane) |
| 29 | I | 3-F | 66 – 69 (from n-hexane) |
| 30 | I | 4-F | 74 – 75 (from n-hexane) |
| 31 | CF₃ | H | 91 – 92 (from n-hexane) |
| 32 | CF₃ | 3-i-C₃H₇ | |
| 33 | CF₃ | 3-t-C₄H₉ | |
| 34 | CF₃ | 3-O-i-C₃H₇ | |
| 35 | CF₃ | 2-F | |
| 36 | CF₃ | 3-F | |
| 37 | CF₃ | 4-F | |

38. N-(fluorodichloromethylthio)-2-methylbenzoic acid-3′-methylanilide
39. N-(fluorodichloromethylthio)-2-methylbenzoic acid-3′-ethylanilide
40. N-(fluorodichloromethylthio)-2-methylbenzoic acid-3′-n-propylanilide
41. N-(fluorodichloromethylthio)-2-methylbenzoic acid-3′-n-butylanilide
42. N-(fluorodichloromethylthio)-2-methylbenzoic acid-3′-tert-pentylanilide
43. N-(fluorodichloromethylthio)-2-methylbenzoic acid-3′-methoxyanilide
44. N-(fluorodichloromethylthio)-2-methylbenzoic acid-3′-ethoxyanilide
45. N-(fluorodichloromethylthio)-2-methylbenzoic acid-3′-n-propoxyanilide
46. N-(fluorodichloromethylthio)-2-methylbenzoic acid-3′-n-butoxyanilide
47. N-(fluorodichloromethylthio)-2-methylbenzoic acid-3′-sec-butoxyanilide
48. N-(fluorodichloromethylthio)-2-methylbenzoic acid-3′-n-pentyloxyanilide
49. N-(fluorodichloromethylthio)-2-methylbenzoic acid-3′-octyloxyanilide
50. N-(fluorodichloromethylthio)-2-methylbenzoic acid-3′-dodecyloxyanilide
51. N-(fluorodichloromethylthio)-2-methylbenzoic acid-3′-allyloxyanilide
52. N-(fluorodichloromethylthio)-2-methylbenzoic acid-3′-propargyloxyanilide
53. N-(fluorodichloromethylthio)-2-methylbenzoic acid-3′-benzyloxyanilide
54. N-(fluorodichloromethylthio)-2-methylbenzoic acid-3′-2-chlorobenzyloxyanilide
55. N-(fluorodichloromethylthio)-2-chlorobenzoic acid-3′-methylanilide
56. N-(fluorodichloromethylthio)-2-chlorobenzoic acid-3′-ethylanilide
57. N-(fluorodichloromethylthio)-2-chlorobenzoic acid-3′-tert-pentylanilide
58. N-(fluorodichloromethylthio)-2-chlorobenzoic acid-3′-ethoxyanilide
59. N-(fluorodichloromethylthio)-2-chlorobenzoic acid-3′-n-propoxyanilide
60. N-(fluorodichloromethylthio)-2-chlorobenzoic acid-3′-allyloxyanilide
61. N-(fluorodichloromethylthio)-2-bromobenzoic acid-3′-methylanilide
62. N-(fluorodichloromethylthio)-2-bromobenzoic acid-3′-ethylanilide
63. N-(fluorodichloromethylthio)-2-bromobenzoic acid-3′-tert-pentylanilide
64. N-(fluorodichloromethylthio)-2-bromobenzoic acid-3′-methoxyanilide
65. N-(fluorodichloromethylthio)-2-bromobenzoic acid-3′-ethoxyanilide
66. N-(fluorodichloromethylthio)-2-bromobenzoic acid-3′-allyloxyanilide
67. N-(fluorodichloromethylthio)-2-iodobenzoic acid-3′-methylanilide
68. N-(fluorodichloromethylthio)-2-iodobenzoic acid-3′-ethylanilide
69. N-(fluorodichloromethylthio)-2-iodobenzoic acid-3′-tert-pentylanilide
70. N-(fluorodichloromethylthio)-2-iodobenzoic acid-3′-allylanilide
71. N-(fluorodichloromethylthio)-2-iodobenzoic acid-3′-isopropenylanilide
72. N-(fluorodichloromethylthio)-2-iodobenzoic acid-3′-methoxyanilide
73. N-(fluorodichloromethylthio)-2-iodobenzoic acid-3′-ethoxyanilide
74. N-(fluorodichloromethylthio)-2-iodobenzoic acid-3′-n-propoxyanilide
75. N-(fluorodichloromethylthio)-2-iodobenzoic acid-3′-n-butoxyanilide
76. N-(fluorodichloromethylthio)-2-iodobenzoic acid-3′-isobutoxyanilide
77. N-(fluorodichloromethylthio)-2-iodobenzoic acid-3′-sec-butoxyanilide
78. N-(fluorodichloromethylthio)-2-iodobenzoic acid-3′-n-pentyloxyanilide
79. N-(fluorodichloromethylthio)-2-iodobenzoic acid-3′-n-hexyloxyanilide In the following examples, the compounds used for comparison purposes were from German Laid-Open Application DOS No. 1,642,224 and had the following formula:

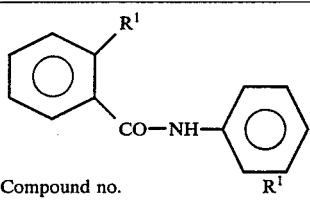

| Compound no. | R¹ |
|---|---|
| 80 | CH₃ |
| 81 | Cl |
| 82 | Br |
| 83 | I |

EXAMPLE 5

Aspergillus niger

The active ingredients are added to a nutrient solution ideally suited for promoting the growth of the fungus *Aspergillus niger* in amounts of 100, 50, 25 and 10 parts by weight per million parts of nutrient solution. 20 ml of the nutrient solution treated in this manner is inoculated with 0.3 mg of Aspergillus spores in 100 ml glass flasks. The flasks are heated for 120 hours at 36° C; the extent of fungus spread, which takes place predominantly on the surface of the solution, is then assessed.

0 = no fungus growth, graduated down to 5 = unchecked growth (surface of nutrient solution completely covered with fungus).

| Active ingredient | Parts of active ingredient per million parts of nutrient solution | | | |
|---|---|---|---|---|
| | 100 | 50 | 25 | 10 |
| 1 | 0 | 0 | 0 | 0 |
| 2 | 0 | 1 | 1 | 2 |
| 10 | 0 | 0 | 0 | 0 |
| 17 | 0 | 1 | 1 | 2 |
| 24 | 0 | 0 | 0 | 2 |
| 80 | 4 | 5 | 5 | 5 |
| 81 comparative | 4 | 5 | 5 | 5 |
| 82 agents | 3 | 4 | 5 | 5 |
| 83 | 3 | 4 | 5 | 5 |
| Untreated (control) | 5 | 5 | 5 | 5 |

EXAMPLE 6

Plasmopara viticola in grapes

Leaves of potted grapes of the Muller-Thurgau variety are sprayed with aqueous dispersions containing 80% (wt%) of active ingredient and 20% of sodium lignin sulfonate (dry basis). 0.1% spray liquors (dry basis) are used. After the sprayed-on layer has dried, the leaves are infected with a zoospore suspension of *Plasmopara viticola*. The plants are first placed for 16 hours in a steam-saturated (moist) chamber at 20° C and then for 8 days in a greenhouse at temperatures of from 20°· to 30° C. The plants are subsequently again placed in the moist chamber for 16 hours to accelerate and intensify spore discharge. The spore sites on the undersides of the leaves are then counted. Untreated infected plants were used as control.

| Active ingredient | Leaf attack after spraying with 0.1% liquor |
|---|---|
| 1 | 0 |
| 2 | 0 |
| 10 | 0 |
| 17 | 0 |
| 24 | 0 |
| 80 | 4 |
| 81 Comparative | 4 |
| 82 compounds | 4 |
| 83 | 4 |
| Untreated (control) | 5 |

0 = no attack, graduated down to 5 = leaves completely covered with fungus

EXAMPLE 7

Botrytis cinerea in peppers

Pepper seedlings of the "Neusiedler Ideal Elite" variety are, after 4 to 5 leaves have developed, sprayed to runoff with 0.1% (wt%) aqueous spray liquors containing 80% of active ingredient and 20% of sodium lignin sulfonate (dry basis). After the sprayed-on layer has dried, the plants are sprayed with a conidial suspension of the fungus *Botrytis cinerea* and placed in a chamber having a temperature of 22° – 24° C and a high relative humidity to ensure optimum growth conditions for the fungus. After 5 days, the disease has spread over the untreated control plants to such a considerable extent that the necroses cover the major portion of the leaves.

| Active ingredient | Leaf necroses after spraying with 0.1% spray liquor |
|---|---|
| 1 | 1 |
| 2 | 1 |
| 10 | 1 |
| 17 | 0 |
| 24 | 0 |
| 6 | 1 |
| 11 | 0 |
| 12 | 0 |
| 15 | 1 |
| 18 | 1 |
| 19 | 1 |
| 80 Comparative | 4 |
| 81 compounds | 3 |
| Untreated (control) | 5 |

0 = no necroses, graduated down to 5 = ⅔ of the leaf surface covered with necroses

EXAMPLE 8

Puccinia coronata in oats

Leaves of oat plants grown in pots are artificially infected with spores of *Puccinia coronata* and placed for 48 hours in a steam-saturated chamber kept at 20° to 25° C. The plants are then sprayed with aqueous liquors which contain, dissolved or emulsified in water, a mixture of 80% of active ingredient and 20% of sodium lignin sulfonate, and placed in a greenhouse at a temperature of from 20° to 22° C and 75 to 80% relative humidity. The extent of fungus spread is assessed after 10 days.

| Active ingredient | Degree of leaf attack after spraying with | | |
|---|---|---|---|
| | 0.1% | 0.05% | 0.025% liquors |
| 2 | 0 | 1 | 2 |
| 10 | 0 | 0 | 2 |
| 17 | 0 | 0 | 2 |
| 24 | 0 | 0 | 2 |
| 15 | 0 | 1 | 2 |
| 25 | 0 | 1 | 1 |
| 80 Comparative | 1 | 2 | 3 |
| 81 | 1 | 2 | 4 |
| 82 compounds | 0 | 1 | 3 |
| Untreated (control) | 5 | 5 | 5 |

0 = no attack, graduated down to 5 = surface

| | Degree of leaf attack after spraying with | | |
|---|---|---|---|
| Active ingredient | 0.1% | 0.05% | 0.025% liquors | of leaves completely covered by fungus

EXAMPLE 9

*Puccinia hordei* in barley

Leaves of barley plants grown in pots are artificially infected with spores of *Puccinia hordei* and placed for 48 hours in a steam-saturated chamber kept at 20° to 25° C. The plants are then sprayed with aqueous liquors which contain, dissolved or emulsified in water, a mixture of 80% of active ingredient and 20% of sodium lignin sulfonate, and placed in a greenhouse at a temperature of from 20° to 22° C and 85 to 80% relative humidity. The extent of fungus spread is assessed after 10 days.

| Active Ingredient | Degree of leaf attack after spraying with | | |
|---|---|---|---|
| | 0.1% | 0.05% | 0.025% liquors |
| 1 | 0 | 1 | 3 |
| 2 | 0 | 0 | 0 |
| 17 | 0 | 1 | 0 |
| 24 | 0 | 0 | 1 |
| 3 | 0 | 0 | 0 |
| 4 | 0 | 0 | 0 |
| 5 | 0 | 2 | 3 |
| 11 | 0 | 0 | 2 |
| 12 | 0 | 0 | 0 |
| 15 | 0 | 1 | 1 |
| 18 | 0 | 0 | 0 |
| 19 | 0 | 0 | 0 |
| 22 | 0 | 0 | 0 |
| 25 | 0 | 0 | 0 |
| 28 | 0 | 0 | 1 |
| 30 | 0 | 1 | 1 |
| Untreated (control) | 5 | | |

0 = no attack, graduated down to 5 = surface of leaves completely covered by fungus

EXAMPLE 10

90 parts by weight of compound 1 is mixed with 10 parts by weight of N-methyl-α-pyrrolidone. A mixture is obtained which is suitable for application in the form of very fine drops.

EXAMPLE 11

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 12

20 parts by weight of compound 10 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 13

20 parts by weight of compound 16 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 14

20 parts by weight of compound 22 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 15

3 parts by weight of compound 1 is intimately mixed with 97 parts by weight of particulate kaolin. A dust is obtained containing 3% by weight of the active ingredient.

EXAMPLE 16

30 parts by weight of compound 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 17

40 parts by weight of compound 10 is intimately mixed with 10 parts of the sodium salt of a phenolsulfonic acid-urea-formaldehyde condensate, 2 parts of silica gel and 48 parts of water. A stable aqueous dispersion is obtained. Dilution in 100,000 parts by weight of water gives an aqueous dispersion containing 0.04 wt% of active ingredient.

EXAMPLE 18

20 parts of compound 16 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. N-(fluorodichloromethylthio)-benzanilides of the formula

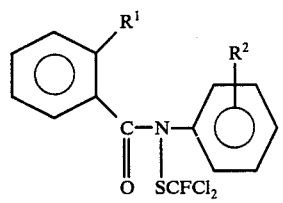

where R¹ denotes halogen, unsubstituted alkyl of 1 to 4 carbon atoms, or halogen-substituted alkyl of 1 to 4 carbon atoms, and R² denotes hydrogen, halogen an alkyl or alkoxy of 1–8 carbon atoms, allyl, isopropenyl, allyloxy, dodecyloxy, propargyloxy, benzyloxy or chlorobenzyloxy.

2. A process for combatting fungi, wherein the objects to be protected from fungus attack, or the fungi, are treated with an N-(fluorodichloromethylthio)-benzanilide of the formula

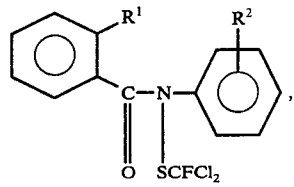

where R¹ denotes halogen, unsubstituted alkyl of 1 to 4 carbon atoms, or halogen-substituted alkyl of 1 to 4 carbon atoms, and R² is defined as set forth in claim 1.

3. N-(fluorodichloromethylthio)-benzanilides selected from the group consisting of N-(fluorodichloromethylthio)-2-iodobenzanilide, N-(fluorodichloromethylthio)-2-iodobenzoic acid-3'-isopropylanilide, N-(fluorodichloromethylthio)-2-bromobenzanilide, N-(fluorodichloromethylthio)-2-bromobenzoic acid-3'-isopropylanilide, N-(fluorodichloromethylthio)-2-bromobenzoic acid-3'-tert-butylanilide, N-(fluorodichloromethylthio)-2-chlorobenzanilide, N-(fluorodichloromethylthio)-2-chlorobenzoic acid-3'-isopropylanilide, N-(fluorodichloromethylthio)-2-chlorobenzoic acid-3'-tert-butylanilide, N-(fluorodichloromethylthio)-2-methylbenzanilide, and N-(fluorodichloromethylthio)-2-methylbenzoic acid-3'-isopropylanilide.

* * * * *